United States Patent [19]
McLeod, Jr.

[11] 4,368,641
[45] Jan. 18, 1983

[54] OUT-OF-ROUND DETECTOR

[75] Inventor: Francis D. McLeod, Jr., Ithaca, N.Y.

[73] Assignee: Powers Manufacturing, Inc., Elmira, N.Y.

[21] Appl. No.: 229,917

[22] Filed: Jan. 30, 1981

[51] Int. Cl.³ ............................................. G01N 29/00
[52] U.S. Cl. ....................................... 73/597; 73/637;
324/58.5 B; 356/428
[58] Field of Search ................ 73/597, 622, 623, 624,
73/628, 637, 640, 104; 356/240, 237, 428;
250/223 B; 324/58.5 B

[56] References Cited

U.S. PATENT DOCUMENTS

| | | | |
|---|---|---|---|
| 3,108,469 | 10/1963 | Dyer et al. | 73/597 |
| 3,289,468 | 12/1966 | Van der Veer et al. | |
| 3,380,293 | 4/1968 | Murphy | 73/624 |
| 3,636,778 | 1/1972 | Huffstetler | 73/622 |
| 3,828,609 | 8/1974 | Furon et al. | 73/622 |
| 4,096,738 | 6/1978 | Rupp et al. | |
| 4,099,418 | 7/1978 | Bennett et al. | |

*Primary Examiner*—James J. Gill
*Attorney, Agent, or Firm*—Seidel, Gonda, Goldhammer & Panitch

[57] ABSTRACT

A container such as a glass bottle is inspected for out-of-round condition while being rotated and moved in line through a test area. A transmitter transducer directs a signal such as a 40 Khz acoustic wave to the outer surface of the bottle. The signal (such as the acoustic wave) reflected from the outer surface of the bottle is received by a receiver transducer. Changes in the phase difference between the transmitted and received signals are detected while the bottle is rotated. The difference between the maximum and minimum values of the changes in phase difference is compared to a threshold value to determine whether an out-of-round condition is tolerable. The bottle is ejected from the line if the difference signal exceeds the threshold value.

28 Claims, 11 Drawing Figures

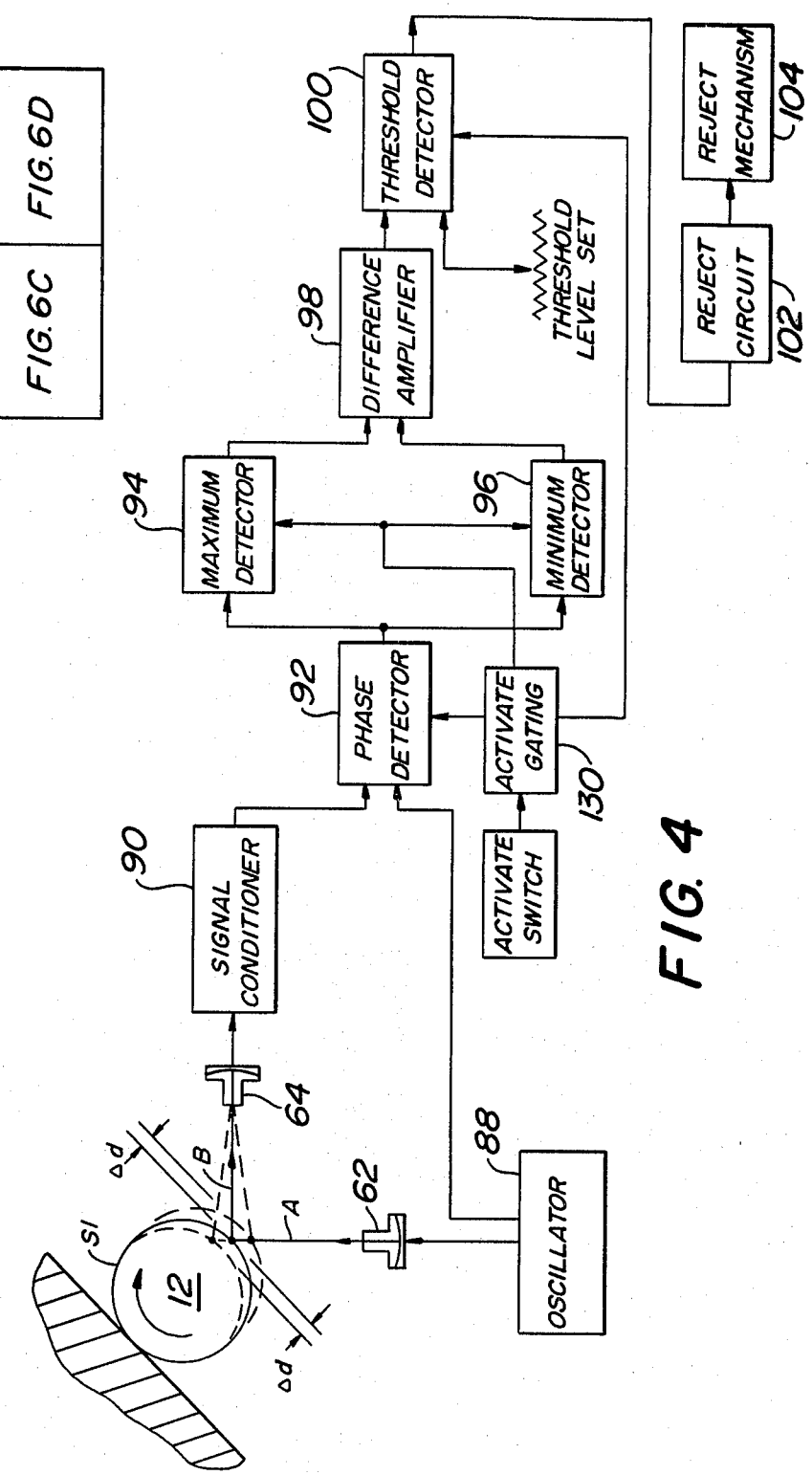

OUT-OF-ROUND DETECTOR

BACKGROUND OF THE INVENTION

The invention is directed to a method and apparatus for inspecting the outer surface of a container such as a glass bottle for out-of-round condition.

In particular, the invention is directed to method and apparatus for inspecting the outer surface of a container using a phase detection technique wherein the phase difference between transmitted and received signals, such as acoustic, optical or microwave signals, is used to provide an indication of the magnitude of the out-of-round condition. The invention has particular application in the inspection of glass bottles for out-of-round condition.

Containers such as glass bottles are formed from molten material. Variations in the heat transfer condition required to produce a rigid container from the molten material may result in malformed containers. A common malformation occurs in the barrel or body portion of the bottle wherein this portion of the bottle is formed in an egg-shaped or other out-of-round condition.

An egg-shaped or out-of-round body condition is undesirable. In pressure containers, such as carbonated beverage bottles, the ideal body shape is cylindrical, i.e., round, to minimize stress. Variations from round result in stress which weakens the container. In labeling a container, an out-of-round condition causes lack of contact between the label and container as well as wrinkling of the label. Further, an out-of-round container is frequently oversized in one dimension, and this results in line jams during filling and processing of the container.

For years, the container processing industry has sought to produce a unit capable of measuring and automatically ejecting from line those containers that are out-of-round beyond tolerable limits. In general, such attempts employed sensors or transducers which mechanically contacted the container surface. Current rates at which containers are formed, however, are so great that it is not practical to maintain mechanical contact between the container and sensor. The use of light, low inertia mechanical sensors does not provide a practical solution to the problem because such sensors tend to become too fragile for survival in the operating environment.

Various acoustic inspection techniques are known for detecting flaws in or characteristics of an object. For example, U.S. Pat. No. 4,096,738 discloses a technique wherein a device ultrasonically tests glass containers by contacting a container and shattering the container if the container is defective. U.S. Pat. No. 4,099,418 discloses an acoustic inspection technique for determining the eccentric characteristics of a tube. At least two acoustic devices are positioned 90° or more apart for the purpose of measuring and comparing container wall thicknesses at the locations of the devices. U.S. Pat. No. 3,289,468 discloses a technique wherein an acoustic transducer disposed along a radius of the object being inspected measures wall thickness. A signal is reflected off the outer surface and the inner surface of the object, with the resultant signals being processed to detect the time interval between reflected pulses.

Heretofore, there has been a need for an accurate and reliable out-of-round inspection unit capable of rapidly and reliably determining an excessive out-of-round condition in the operating environment of the container processing plant while being relatively simple to operate and service.

SUMMARY OF THE INVENTION

A container to be inspected for out-of-round condition is rotated while a signal is directed to an area of the outer surface of the container. As the container is rotated, reflections of the signal off the outer surface of the container are received, and changes in the phase difference between the transmitted and received signals are computed. Both the maximum and minimum values of the changes in phase difference are determined. The difference between the maximum and minimum values is compared to a predetermined threshold to determine an excessive out-of-round condition. The container is automatically ejected from the line if the out-of-round condition is determined to be excessive.

The invention permits the accurate and reliable determination of out-of-round condition of a container in the working environment of the container processing plant.

In addition, the invention permits the rapid determination of out-of-round condition and, if necessary, automatic ejection of excessively out-of-round containers without interrupting line flow during production and processing of the containers.

Further, the invention eliminates the need for mechanical contact between the container body and sensors during out-of-round inspection and greatly simplifies the set-up and servicing of sensors or transducers by operating personnel.

Other advantages of the invention appear hereinafter.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 4 is a block diagram of the out-of-round detector electronics.

FIGS. 5 and 6A, 6B, 6C and 6D comprise a detailed schematic of the detector electronics.

DETAILED DESCRIPTION OF THE INVENTION

Figure 1:
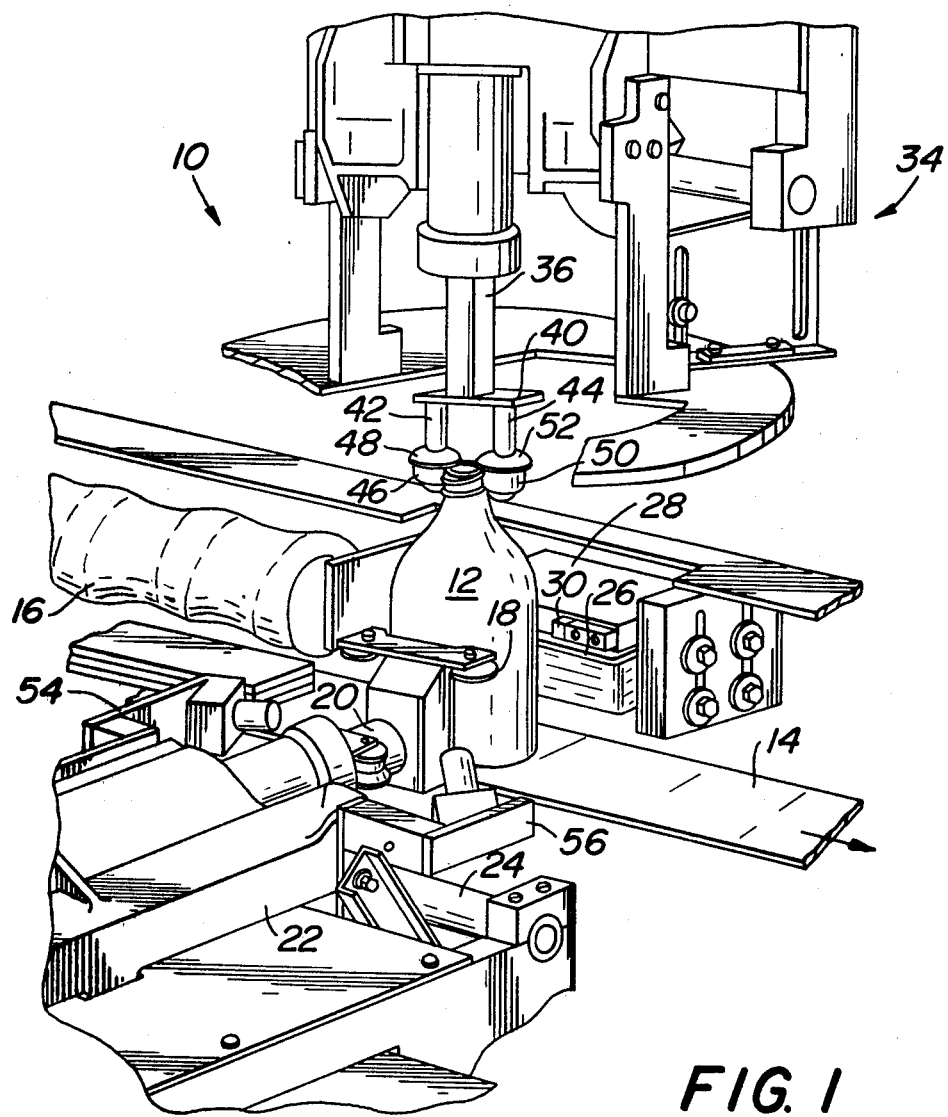
FIG. 1 is a perspective view of a preferred embodiment of the out-of-round detector of the present invention wherein acoustic signals are employed.

Referring to the drawings in detail, wherein like numerals indicate like elements, there is shown in FIG. 1 an acoustic out-of-round detector designated generally as 10 which is a preferred embodiment of the present invention.

As shown in FIG. 1, a container such as a glass bottle 12 to be inspected for out-of-round condition is transported on a linear conveyor 14 of conventional construction. The containers are spaced and sequentially moved in line through a test area by a feed screw 16. As the container 12 enters the test area, it is engaged by a pair of spaced rollers 18 on a horizontal plunger 20 mounted on a horizontally movable carriage 22. While one pair of rollers 18 is illustrated, use of two pairs of rollers disposed one above the other may be utilized with certain types of containers. The carriage 22 is mounted for movement along the axes of a pair of shafts 24 (only one of which is illustrated).

The rollers 18 contact the container 12 and move with the carriage 22 while pressing the container 12 against a horizontally moving endless belt 26. The belt 26 presents a substantially vertical planar surface which contacts the container body to rotate the container as it moves through the test area. The belt 26 rotates the container fast enough to make at least one full revolution while the container passes through the test area. The belt 26 extends around guide rollers (not shown) in a housing 28. A brake block 30 of a material such as rubber having an angled cam face is supported by the housing 28. The brake block 30 causes the container to lose contact with belt 26, stopping the container from rotating. Block 30 is located at the downstream end of the test area.

The belt 26 can move either opposite the direction of conveyor movement or with the direction of conveyor movement. The belt 26 is driven by a variable speed motor whose speed can be adjusted to provide the required rotation.

The apparatus described above is in all material respects identical with that described in U.S. Pat. No. 3,690,456 issued Sept. 12, 1972 and U.S. Pat. No. 3,557,950 issued Jan. 26, 1971. The disclosure in said patents is incorporated herein by reference.

A carriage 34 having a downwardly extending plunger 36 is mounted for reciprocating horizontal movement along a pair of shafts (not shown). The plunger 36 is mounted for vertical movement with respect to the carriage 34. The carriages 22 and 34 are moved in synchronism through the test area at constant speed in the direction of travel of the conveyor 14 and return at a substantially sinusoidal rate after completion of the inspection of the container 12. The mechanism for reciprocating the carriages 22 and 34 in timed relation with the screw 16 as well as the mechanism for moving the plunger 36 downwardly at the beginning of the test area and upwardly at the end of the test area are described in above-mentioned U.S. Pat. No. 3,557,950 as well as U.S. Pat. No. 3,387,704 issued June 11, 1968. The disclosures in said patents are incorporated herein by reference. Further description of the mechanism for reciprocating the carriages and the mechanism for moving the plunger is deemed unnecessary. Each of the plungers 20 and 36 is cammed or spring-biased into contact with the container 12 at the beginning of the stroke of the carriages and is biased away from the container at the end of the carriage strokes.

A mounting plate 40 is secured to the lower end of the plunger 36. Plate 40 supports parallel shafts 42 and 44. The axes of shafts 42 and 44 form a straight line parallel to the side edge of the conveyor 14.

A finish-engaging roller 46 is rotatably supported by shaft 42 and has a flange 48 adapted to overlie and contact the end face of the finish on the container 12. Roller 46 is made from a rubber or plastic material so as not to damage the finish.

A roller 50, comparable to roller 46, is rotatably supported by shaft 44. Roller 50 is provided with a flange 52 comparable to flange 48. The flanges 48 and 52 hold the container 12 downwardly against any vertical forces generated by rotation of the container resulting from contact with the belt 26.

The rollers 46 and 50 are supported in a position whereby the rollers 18 move the container 12 such that the end face of the finish of the container contacts rollers 46 and 50 at the same time that the body of the container engages the belt 26. The stroke of the plunger 20 and the transverse location of the feed screw 16 and belt 26 are selectively adjustable to accommodate various sized containers. The plunger 20 may be a spring-biased plunger as disclosed in said U.S. Pat. No. 3,557,950, and plunger 36 may be a spring-biased plunger as disclosed in U.S. Pat. No. 3,387,704.

The rollers 18 engage the container 12 at an elevation which is above the elevation of the belt 26 and below the elevation of the rollers 46 and 50. The rollers 18, 46 and 50 are so positioned that the container 12 is held in a vertical disposition so as to avoid as far as possible any loss of stability of the container.

The structural features described thus far are as disclosed in said U.S. Pat. No. 3,690,456.

Figure 2:
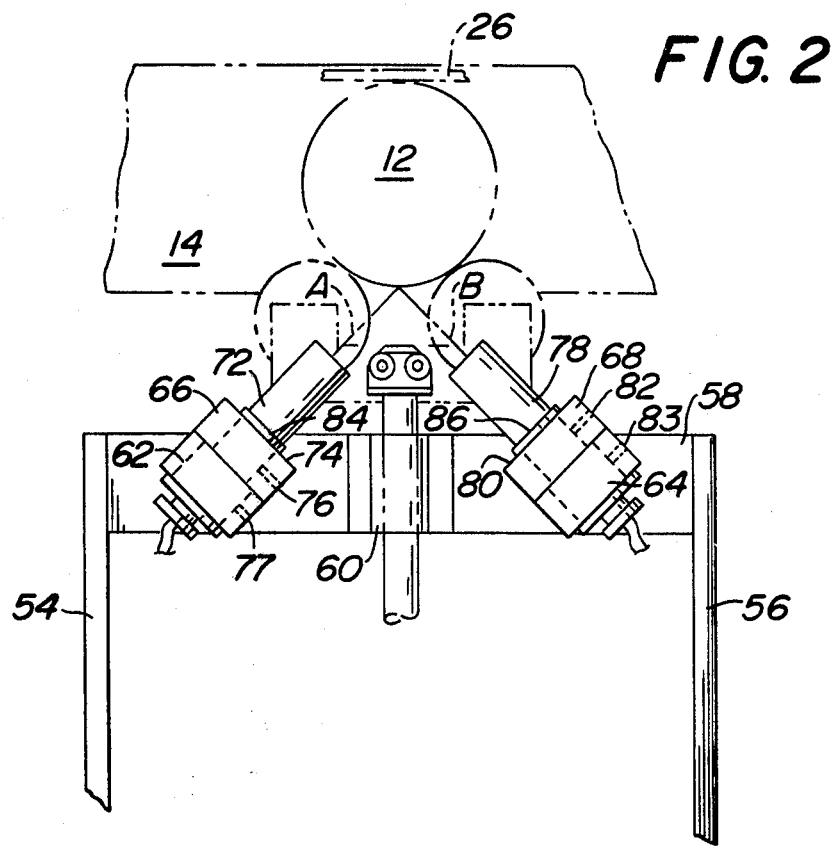
FIG. 2 is a plan view of the horizontal carriage and the acoustic transducers.
Figure 3:
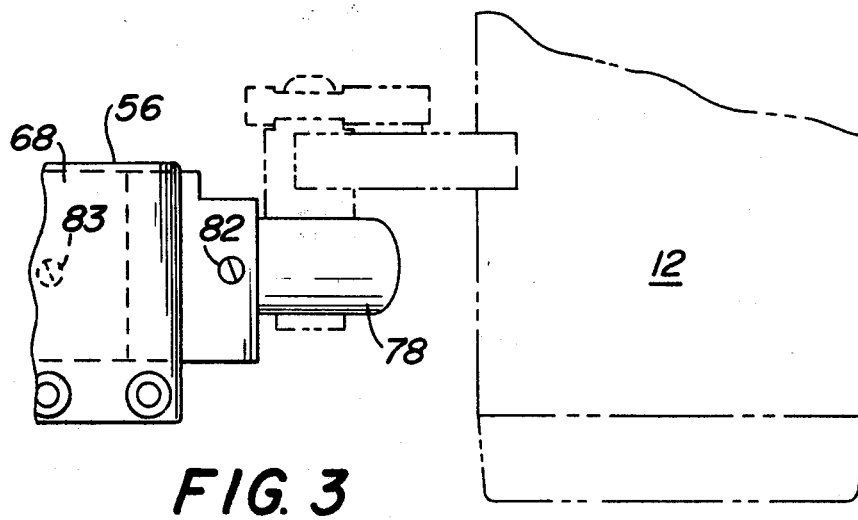
FIG. 3 is a side elevation of the horizontal carriage and transducers.

Referring to FIGS. 2 and 3, a pair of side plates 54, 56 are screw fastened to the carriage 22. A shelf or platform 58 is fastened by means of screws to the plates 54, 56. The shelf 58 is provided with an intermediate opening 60 which is sized to accommodate the plunger 20.

A pair of transducers 62, 64 such as MK 109 C (MASA Products) electro-acoustic transducers are mounted respectively in housings 66, 68 which are secured by screws to the shelf 58. The housings 66 and 68 are angled so as to face an area of the body of the container 12 which is approximately diametrically opposite to the area of contact of the container and the belt 26. This is indicated by the intersecting broken lines A, B in FIG. 2.

The transducer 62 is located within housing 66 and is provided with an acoustic tube 72 which protrudes through the end face 74 of housing 66. The transducer 62 and tube 72 are aligned with broken line A in FIG. 2 by means of set screws 76, 77.

The transducer 64 is located within housing 68 and is provided with an acoustic tube 78 which protrudes through the end face 80 of housing 68. The transducer 64 and tube 78 are aligned with the broken line B in FIG. 2 by means of set screws 82, 83.

The tubes 72, 78 are supported in their aligned positions on housings 66, 68 respectively by means of push-on rings 84 and 86.

MEASUREMENT OF CHANGE IN PHASE DIFFERENCE

Referring to FIG. 4, the transducer 62 is electrically coupled to an oscillator 88 such as a 40 Khz oscillator. The oscillator 88 drives the transducer 62 which propagates an acoustic signal incident on the body of container 12 at the area of intersection of lines A and B.

The acoustic signal transmitted by transducer 62 is reflected by the outer surface of the container 12 along the path indicated by line B to the transducer 64. The transducer 64 receives the reflected acoustic signal and converts the same to an electric signal which is filtered and amplified by signal conditioner 90.

The output of the signal conditioner 90 is fed to a phase detector 92. The output of the oscillator 88 is also fed to the phase detector 92.

Variations $\Delta d$ in the diameter of the container 12 due to out-of-round condition cause corresponding variations in the total path length A+B traveled by the acoustic signal from transducer 62 to the container surface and onto tranducer 64. Assuming identical angles of incidence and reflection of approximately 45°, as shown in FIG. 4, relatively small variations $\Delta d$ in the container diameter (compared to the distances A and B) cause a change in the path length A+B of approximately $\Delta d\sqrt{2}$. Other spatial configurations, i.e., angles of incidence and reflection, can of course be employed for the transducers 62 and 64 within the spirit and scope of the invention. In such cases, relatively small variations in the container diameter cause proportional changes in the path length A+B.

The lapse in time between occurrence of the oscillator output signal and the corresponding output signal delivered by the signal conditioner 90 is referred to hereafter as "phase difference". This phase difference varies in proportion to changes in the path length A+B. As previously indicated, the path length A+B changes with the container diameter. The phase detector 92 detects the change in phase difference and generates a signal having a magnitude proportional to the change, hence proportional to the change in container diameter along the container surface.

The output of the phase detector 92 is fed to a maximum peak detector 94 and a minimum peak detector 96. The maximum peak detector 94 is a buffered peak detector which detects the maximum peak change in phase difference between the inputs to phase detector 92 due to an out-of-round condition wherein a portion of the container surface has a lesser diameter than the diameter of the ideal cylindrical body. Such an out-of-round condition results in increased total path length A+B between the container and transducers.

The minimum peak detector 96 is also a buffered peak detector. The peak detector 96 detects the minimum peak change in phase difference between the inputs to phase detector 92 due to an out-of-round condition wherein a portion of the container surface has a diameter greater than the diameter of the ideal cylindrical body. Such out-of-round condition results in reduced total path length A+B.

The difference between the maximum and minimum peak values, as indicated by the outputs of detectors 94 and 96 respectively, is detected by difference amplifier 98. The output generated by difference amplifier 98, then, provides a measure of the out-of-round condition of the container.

The output of difference amplifier 98 is compared by a threshold detector 100 to a predetermined threshold value to determine whether the container should be passed (out-of-round condition tolerable) or rejected (excessive out-of-round condition). If the threshold value is exceeded, indicating an excessive out-of-round condition, the threshold detector generates a reject signal which triggers a reject circuit 102. The reject circuit 102 operates a reject mechanism 104 such as an electromagnetically actuated ejector paddle located downstream of the test area for ejecting containers from the line as described in U.S. Pat. No. 3,557,950.

DETAILS OF ELECTRONICS

Figure 6A:
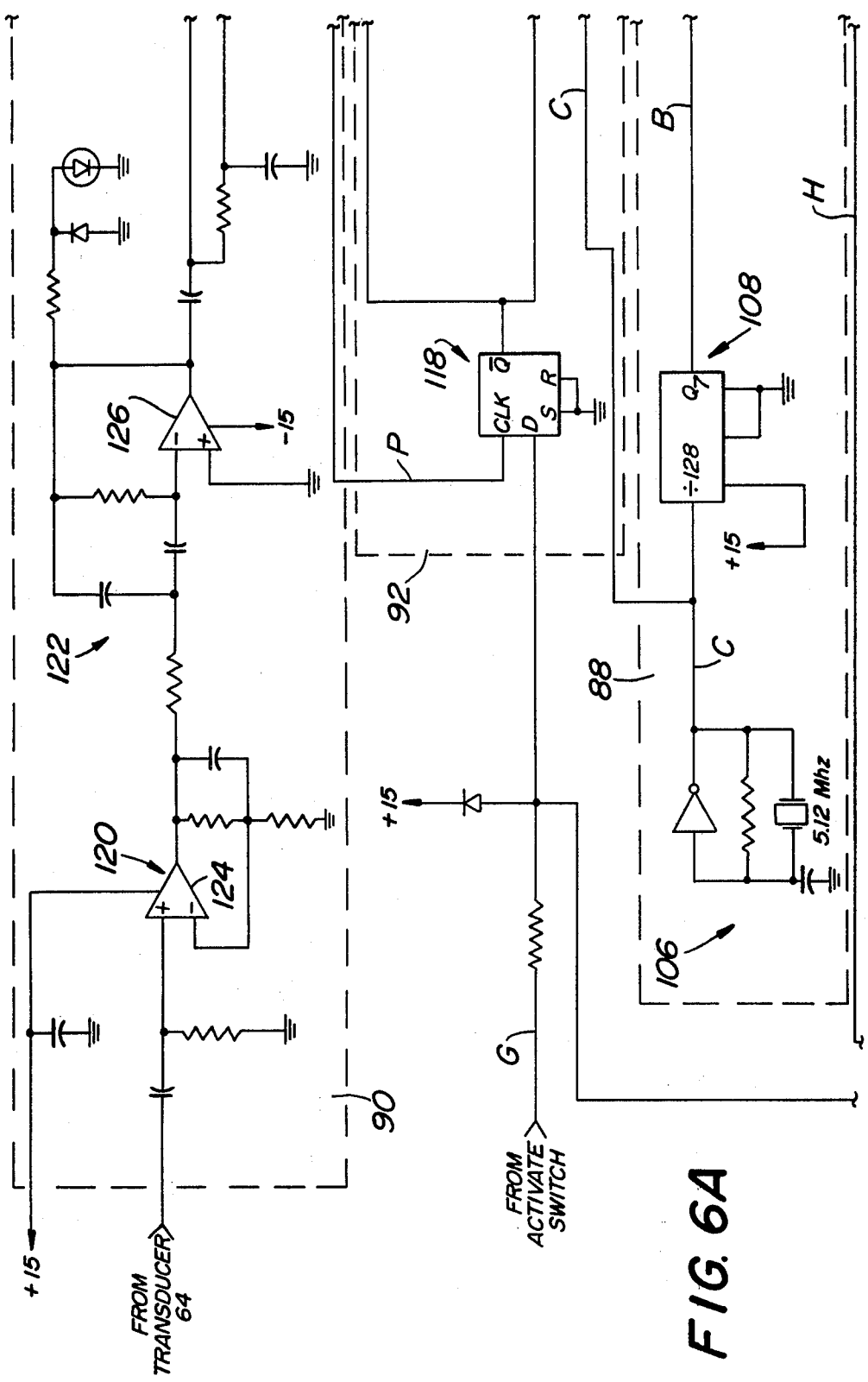
Figure 6B:
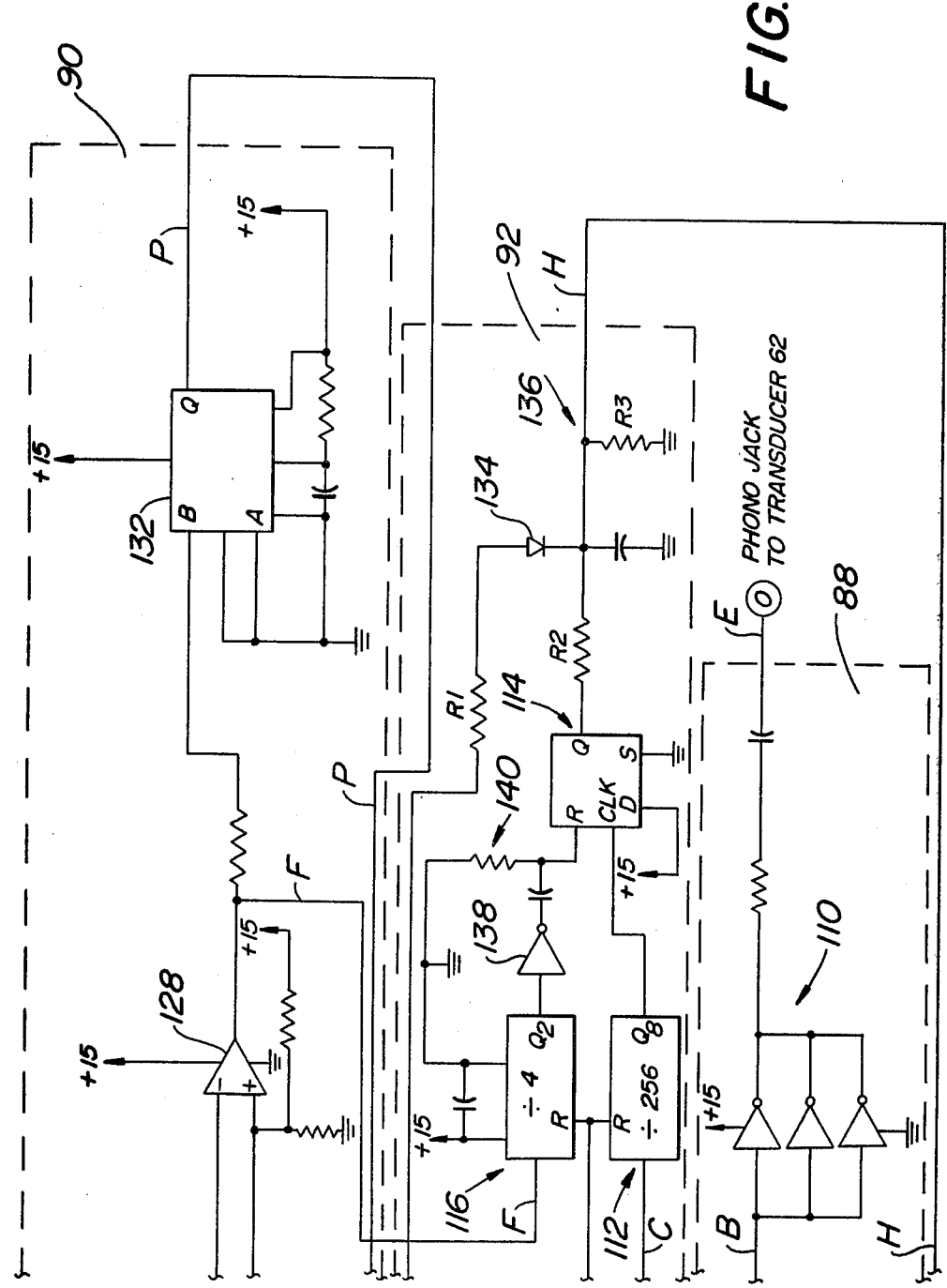
Figure 6C:
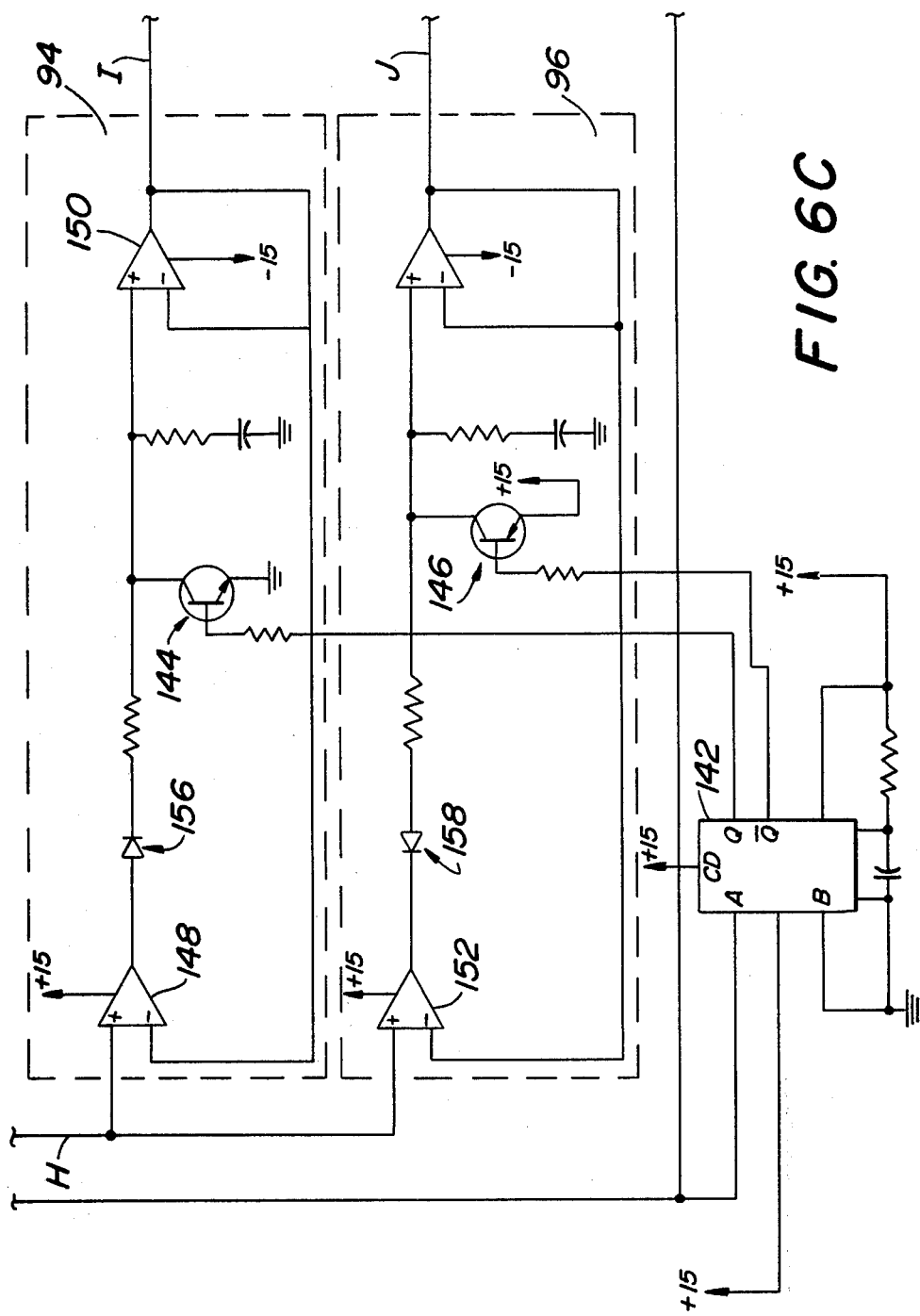
Figure 6D:
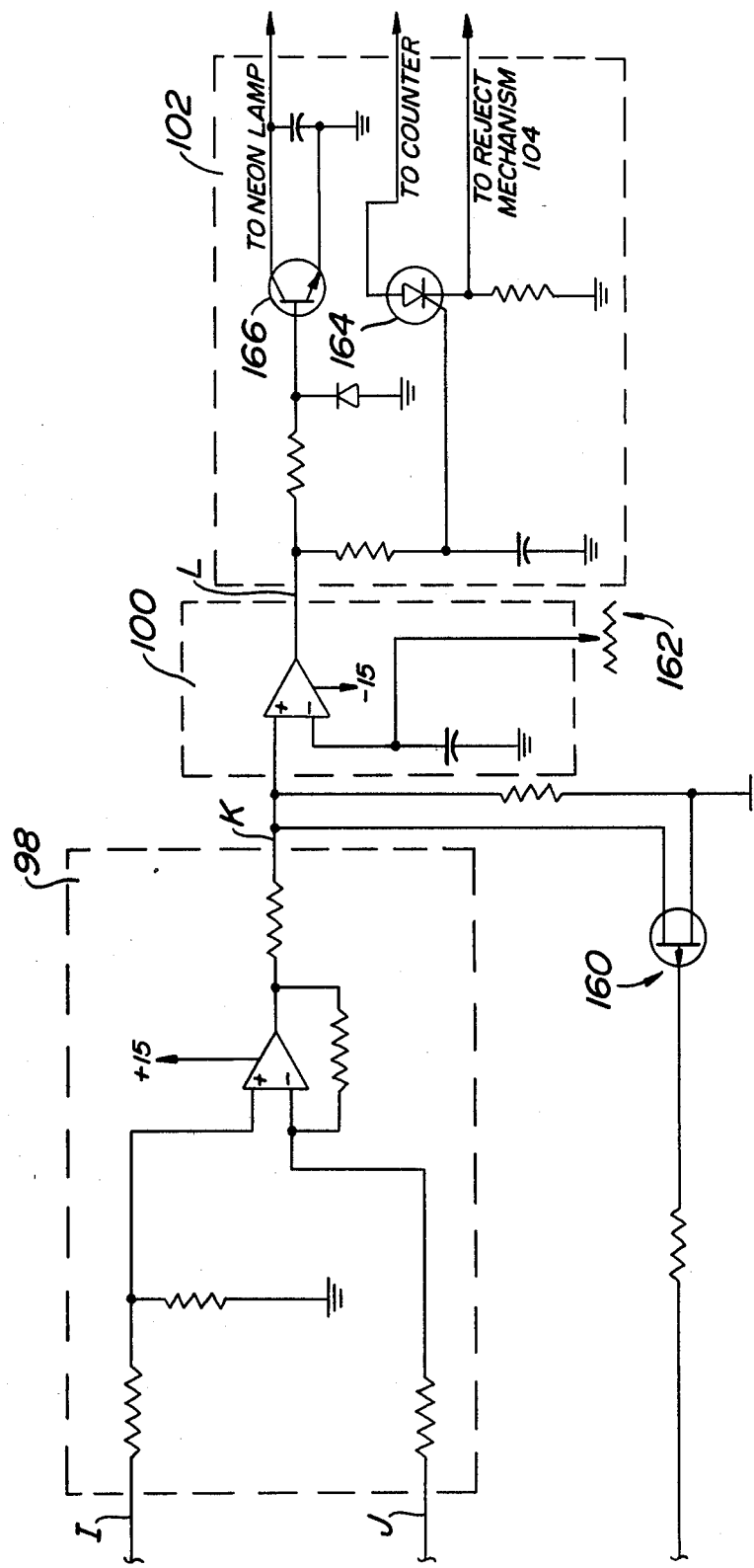

Referring to FIGS. 5 and 6A–6D, the 40 Khz oscillator 88 comprises a crystal oscillator circuit 106 which produces a 5.12 Mhz pulse train on line C. See FIG. 6A. The pulse train is passed to a divide by 128 counter 108, such as an integrated circuit (I.C.) 4040 counter. The counter 108 produces a reduced frequency, 40 Khz pulse train at the line B input to a bank of inverter/drivers 110. See FIG. 6B. The drivers 110 may be I.C. 4069 drivers taken on a common chip as indicated in FIG. 6B. The output E of oscillator 88 is a 40 Khz pulse train which drives the transmitter transducer 62.

The 5.12 Mhz pulse train on line C is passed to the input of a divide-by-256 counter 112 in phase detector 92. See FIG. 6B. The output of counter 112 is a 10 Khz pulse train which controls the CLK input of a flip-flop 114. The flip-flop 114 serves as a "phase meter" as described in detail hereafter. The flip-flop 114 may be a 4013 flip-flop. The reset input R of flip-flop 114 is controlled by the output of a divide-by-4 counter 116. Counters 112 and 116 may be I.C. 4040 counters whose reset inputs R are commonly connected on a single chip. The reset inputs of counters 112, 116 are controlled by the output of a flip-flop 118, such as an I.C. 4013 flip-flop. Flip-flop 118 serves as a "timing" control as described in detail below, and is referred to hereafter as "timing" flip-flop 118.

As illustrated in FIGS. 6A and 6B, the phase detector 92 comprises two counter channels. One channel, comprising counter 112, is responsive to the 5.12 Mhz pulse train supplied by crystal oscillator circuit 106 on line C. The other channel comprises counter 116 which is responsive to the filtered, amplified signal supplied on line F by the signal conditioner 90.

More specifically, the filtered, amplified signal provided on line F is based on the received, transduced acoustic signal reflected from the outer surface of bottle 12. The received, transduced signal is passed through amplifier-filter circuits 120, 122 comprising difference amplifiers 124, 126. See FIG. 6A. Difference amplifiers 124, 126 may be TL082 amplifiers. The output of amplifier 126 is passed to the inverting input of a third difference amplifier 128 such as a NE531 amplifier. The output of amplifier 128 is a squared, logic compatible signal which controls the divide-by-4 counter 116 in phase detector 92.

In operation, an "activate" switch, see FIG. 4, which may be a microswitch or similar device positioned at the test area to sense the presence of a container, provides a pulse signal at line G (FIG. 6A). The width of the pulse signal is determined by the length of time that the container is present at the test area. At the leading edge of the pulse produced by the "activate" switch, the D input of "timing" flip-flop 118 is raised, and the pulse output of a one shot 132 (FIG. 6B) appearing at the CLK input of flip-flop 118, causes the flip-flop output $\overline{Q}$ to release the reset on counters 112 and 116. The one shot 132 may be an I.C. 4528 one shot. One shot 132 produces a pulse train of fixed width pulses on line P in response to the amplified, filtered 40 Khz signal produced by amplifier 128. The output of "timing" flip-flop 118 also controls a diode 134 connected to a RC integrator 136. When the output of flip-flop 118 releases the reset on counters 112, 116, it also reverse biases the diode 134 thereby "opening" the diode. As previously indicated, these operations occur at the leading edge of the pulse signal produced by the "activate" switch, that is, when the container 12 enters the test area.

The counters 112, 116 begin counting in response to their respective inputs. Counter 116 produces a 10 Khz pulse train which is inverted by inverter 138, which may be an I.C. 4069 inverter, and passed through RC differentiator circuit 140 to the reset input R of "phase meter" flip-flop 114. The leading edge of the 10 Khz pulse produced by counter 116 causes inverter 138 to release the reset on flip-flop 114, enabling the flip-flop to respond to pulses generated by counter 112 at the CLK input of the flip-flop. The pulses generated by counter 112 are 10 Khz pulses which cause the Q output of flip-flop 114 to change state and hold the new state as long as the reset on flip-flop 114 is released. The RC integrator 136 integrates the step change in output of flip-flop 14, producing a ramp-type signal at the line H output of phase detector 92.

After counter 116 counts 4 pulses at the line F input, the output of the counter changes state, causing inverter 138 to reset "phase meter" flip-flop 114. The output of flip-flop 114, therefore, produces a pulse whose width is determined by the trailing edge of the counter 116 output and the leading edge of the counter 112 output. The occurrence of the leading edge of the counter 112 output is "fixed" in time (oscillator 106 being free-running) whereas the occurrence of the trailing edge of the counter 116 output depends on the time of reception of the acoustic signal reflected off bottle 12. Accordingly, the pulse output of flip-flop 114 has a variable pulse width dependent on the path length A+B and, therefore, on the variations in container diameter due to out-of-round surface. Thus, the level of the signal on line H provides an indication of the degree of out-of-round of the container.

When the container enters the test area, the pulse signal generated on line G by the "activate" switch triggers a one shot 142 which controls the gating of maximum and minimum detectors 94 and 96 and threshold detector 100. See FIG. 6C. One shot 142, like one shot 132, may be an I.C. 4528 one shot. The Q output of one shot 142 controls a gating transistor 144 of the 2N3904 type whereas the $\bar{Q}$ output of the one shot controls a gating transistor 146 of the 2N3906 type. Gating transistors 144, 146 serve to reset the maximum and minimum detectors 94, 96.

The detectors 94 and 96 are buffered peak detectors of a type known in the art. Detector 94 includes difference amplifiers 148 and 150 such as TL082 amplifiers. Detector 96 includes like amplifiers 152 and 154. The detectors 94, 96 also include oppositely poled diodes 156, 158.

Detector 94 detects rising voltages on line H, and the output I of the detector remains at the voltage level on line H at the trailing edge of the previous pulse produced by flip-flop 114 unless the voltage level on line H has increased beyond that level. Thus, the detector 94 detects successive peaks of the line H signal, holding the highest or maximum peak. Minimum detector 96 functions in like manner to detector 94. Detector 96, however, detects minimum peaks whereas detector 94 detects maximum peaks. Thus, detector 96 holds the lowest or minimum peak for the line H signal. See FIG. 8. The difference between the outputs I, J of detectors 94, 96 therefore represents the summed maximum deviations in path length A+B caused by out-of-round of the container surface due to increases and decreases in container diameter.

As previously indicated, gating transistors 144, 146 reset detectors 94, 96 in response to the Q and $\bar{Q}$ outputs of one shot 142 at the leading edge of the pulse signal generated on line G by the "activate" switch. See FIG. 6C. This occurs when the container 12 enters the test area. The one shot 142 generates complementary, brief reset pulses at its Q and $\bar{Q}$ outputs which turn gating transistors 144, 146 "on" for the duration of each pulse. Gating transistor 144 forward biases diode 156 therefore resetting the output of difference amplifier 148 to zero while gating transistor 146 forward biases diode 158 to reset the output of difference amplifier 152 to +15 volts. At the trailing edges of the complementary pulse outputs of one shot 142, the gating transistors 144, 146 release the reset on detectors 94, 96, permitting the detectors to function as previously described.

The maximum peak detected by detector 94 appears at the line I output while the minimum peak detected by detector 96 appears at the line J output. The difference between the maximum and minimum peaks is taken by the difference amplifier 98 which generates an output signal on line K representative of the difference. See FIG. 6D. A gating FET 160 remains "open" during the interval of the pulse signal generated on line G to permit the difference signal on line K to pass to the non-inverting input of the threshold detector 100. At the end of the pulse signal on line G, when the container 12 leaves the test area, the gating FET 160 "closes" to clamp the line K output of difference amplifier 98 to zero thereby resetting the difference amplifier. The FET 160 therefore maintains the difference amplifier 98 reset between pulses on line G, i.e., until the next container enters the test area.

The threshold detector 100 compares the difference signal on line K to a preset threshold level selected by manipulation of the threshold level set potentiometer 162. The threshold is chosen to enable the detector 100 to provide an output signal on line L when the difference signal on line K indicates an excessive out-of-round condition. The line L output signal operates the reject circuit 102, causing the circuit to activate the reject mechanism 104 for an excessive out-of-round condition.

Specifically, the line L signal gates a SCR 164, such as a 2N2324 SCR, "on" to advance a counter (not shown) one count while activating the reject mechanism 104. See FIG. 6D. As each excessively out-of-round container is ejected by mechanism 104, then, a count is maintained of the total number of ejected containers. The line L signal also gates a transistor 166, such as a MPSA 42 transistor, "on" to activate a Neon lamp (not shown) thereby providing a warning signal to the operator.

Figure 7:
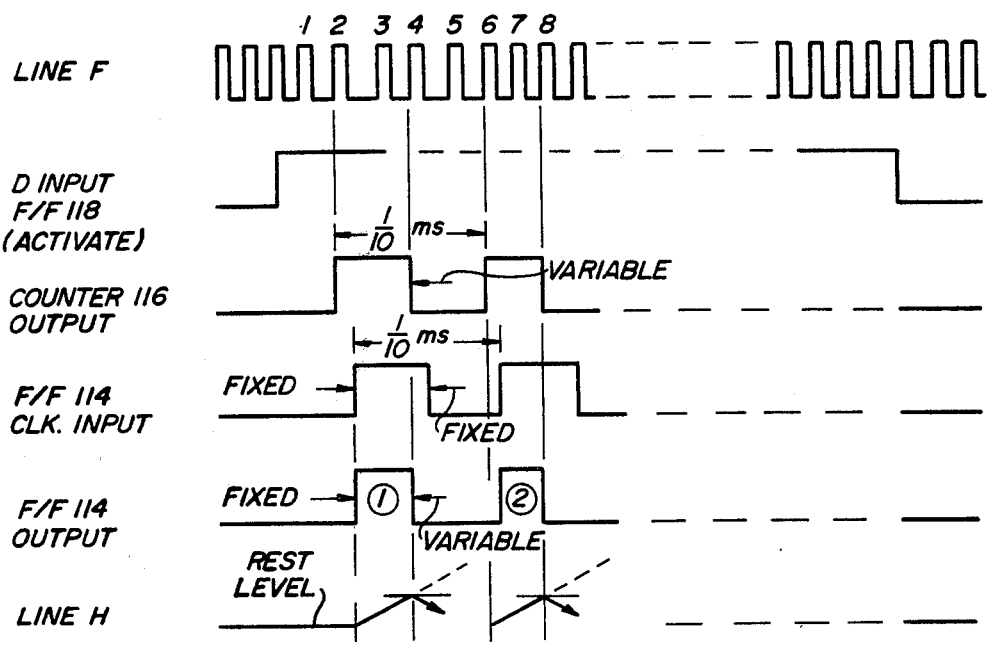
FIG. 7 is a timing diagram of the waveforms appearing at certain of the component inputs and outputs.
Figure 8:
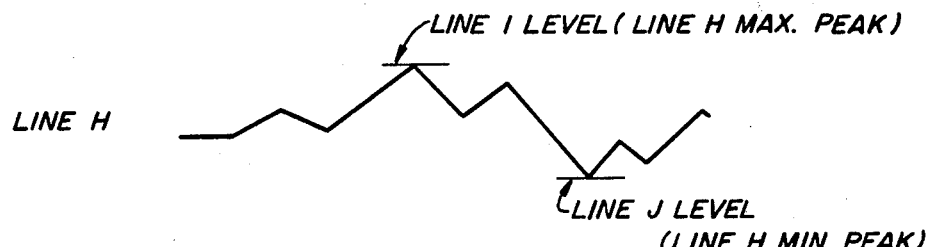
FIG. 8 is a diagram representative of a changing signal at the maximum and minimum detector outputs.

When a container leaves the test area, as indicated by the trailing edge of the pulse signal on line G, gating FET 160 resets the difference amplifier 98 (as already explained) and the D input of the "timing" flip-flop 118 (FIG. 6A) changes state causing the output of the flip-flop to reset counters 112 and 116 in response to the pulses appearing at the CLK input of the flip-flop. This in turn removes the signal at the CLK input to "phase meter" flip-flop 114 (FIG. 6B) while maintaining the flip-flop reset. The RC integrator 136 seeks a rest voltage determined by resistors R1, R2, R3, forward biased diode 134, and the outputs of flip-flops 118 and 114. The foregoing is illustrated in FIGS. 7 and 8.

It should be apparent that variations in the pulse width of the output of "phase meter" flip-flop 114 represent variations in the phase difference between the transmitted and received acoustic signals, hence deviations in the roundness of the outer surface of the container 12. In FIG. 7, successive pulses "1" and "2" having different widths are shown at the output of flip-flop 114. Although a pulse width detection technique has been described herein, other equivalent techniques may also be employed to detect such variations in phase difference within the spirit and scope of the invention.

It should be appreciated that the range of variations in phase difference detectable by the present invention is basically determined by the frequency of the output pulses generated by counter 116, that is, by the number of stages of the counter. Representing the number of stages of the counter as N, the counter permits an N times greater change in path length A+B to occur before the transmitted and received acoustic signals shift a full cycle with respect to each other to cause a discontinuity in the output of RC integrator 136 at the range limit.

Although the detection or computation of variations in phase difference has been described in connection with divide by 4 and divide-by-256 counters 116 and 112, it should be apparent that counters having other numbers of stages may also be employed within the spirit and scope of the invention, it only being required that the output of the counters have the same frequency.

Although the invention has been described in terms of the preferred embodiment wherein a 40 Khz continuous acoustic signal is employed as the reference for phase detection purposes, it should be appreciated that other types of acoustic signals and other types of energy sources, such as optical and microwave, may also be employed within the spirit and scope of the invention.

For example, referring to the block diagram in FIG. 4, an acoustic "pulse echo" technique may be employed wherein the transmitter transducer 62 transmits discrete pulses of acoustic energy at regular intervals of time along path A to the container surface. The acoustic pulses are reflected by the container surface and directed along path B to the receiver transducer 64. The transducer 64 output would be conditioned (squared and made logic compatible) by signal conditioner 90. The time delay ("phase difference") between transmission and reception of each acoustic pulse owing to changes in the total path length A+B is computed by the phase detector 92, and the maximum and minimum peaks of the phase detector output is detected (by maximum and minimum detectors 94, 96), combined (by difference amplifier 98) and the result compared to the preset threshold (by threshold detector 100) as previously described.

In addition, optical or microwave signals may be employed in lieu of acoustic signals in practicing the invention. Thus, a monochromatic optical signal source such as a laser may be employed as the transmitter transducer 62 to transmit an optical signal to the surface of the container being inspected. A receiver transducer 64 such as a photodiode receives the optical signal reflected from the container surface and provides an electrical output signal which is conditioned by the signal conditioner 90. The phase difference between the received optical signal and the transmitted signal is computed by the phase detector 92, and the remaining signal processing and detection steps are performed as previously described. Due to the shorter wavelength of the optical signal (as compared to an acoustic signal), the use of optical signals on the inspection process would be especially suited for inspection of relatively small containers having limited size inspection surfaces.

A microwave technique can also be used in practicing the invention wherein a Gunn diode serves as the transducer 62 to transmit a microwave signal to the container surface. The microwave signal reflected from the container surface is received by a microwave receiver transducer 64, and the output of the microwave transducer is conditioned by signal conditioner 90 and fed to phase detector 92 for processing as already described.

The present invention may be embodied in other specific forms without departing from the spirit or essential attributes thereof and, accordingly, reference should be made to the appended claims, rather than to the foregoing specification, as indicating the scope of the invention.

I claim:

1. A method of detecting an out-of-round condition in a container, comprising:
    directing a signal to a surface of the container, said signal being reflected by said surface,
    causing relative rotation between the container and signal,
    detecting variations in phase difference between the signal directed to the container surface and the reflected signal,
    determining maximum and minimum variations in phase differences between the directed and reflected signals, and
    determining whether there is an excessive out-of-round condition of the container by comparing the difference between said maximum and minimum variations to a predetermined threshold value.

2. The method according to claim 1 wherein said directed and reflected signals are acoustic signals.

3. The method according to claim 1 wherein said directed and reflected signals are optical signals.

4. The method according to claim 1 wherein said directed and reflected signals are microwave signals.

5. The method according to claims 1 or 2 including rotating the container while directing said signal to the container surface.

6. The method according to claim 5 wherein said step of rotating said container includes rotating the container while against a contacting surface, and wherein said step of directing said signal to the container surface includes directing the signal to an area on the container surface which is approximately diametrically opposed to the area of contact between the container surface and the contacting surface.

7. The method according to claim 5 including the step of operating a reject mechanism to eject the container if the threshold value is exceeded.

8. A method of detecting an out-of-round condition in a container, comprising:
    transmitting a signal such that the signal is incident on a surface of the container, said signal being reflected by said surface,
    causing relative rotation between the container and signal,
    receiving the signal reflected from the surface of the container,
    computing maximum and minimum variations of the difference in phase between the transmitted and received signals,
    determining the difference between said maximum and minimum variations, and
    determining whether there is an excessive out-of-round condition of the container by comparing said difference to a pre-established threshold value.

9. The method according to claim 8 wherein said incident and reflected signals are acoustic signals.

10. The method according to claim 8 wherein said incident and reflected signals are optical signals.

11. The method according to claim 8 wherein said incident and reflected signals are microwave signals.

12. The method according to claims 8 or 9 including transmitting said signal and receiving said reflected signal while rotating said container.

13. The method according to claims 8 or 9 including rotating said container against a contacting surface and directing the transmitted signal to an area on the the container surface approximately diametrically opposed to the area of contact between the container and the contacting surface.

14. The method according to claims 8 or 9 including the step of ejecting the container if said difference exceeds the pre-established threshold value.

15. Apparatus for detecting an out-of-round condition in a container, comprising:
  means for directing a signal towards a surface of the container, said signal being reflected by said surface,
  means for causing relative rotation between the container and signal,
  means for receiving the signal reflected from the surface of the container,
  means for detecting variations in the phase difference between the directed and received signals,
  means for detecting maximum and minimum peaks of said detected variations in phase difference,
  means for detecting the difference between said maximum and minimum peaks, and
  means for comparing said difference between the maximum and minimum peaks to a pre-established threshold value representative of an excessive out-of-round condition.

16. Apparatus according to claim 15 wherein said directed and reflected signals are acoustic signals.

17. Apparatus according to claim 15 wherein said directed and reflected signals are optical signals.

18. Apparatus according to claim 15 wherein said directed and reflected signals are microwave signals.

19. Apparatus in accordance with claims 15 or 16 including means for detecting the presence of said container at a test area, and means for resetting the output of said means for detecting the difference between said maximum and minimum peaks if said container is not present at said test area.

20. Apparatus in accordance with claims 15 or 16 wherein said means for detecting variations in the phase difference between the directed and received signals includes a first counter for counting directed signals, a second counter for counting the received acoustic signals, means for producing a pulse having a width determined by the counts maintained by said first and second counters, and means for integrating said pulse to provide a signal indicative of said variations in phase difference.

21. Apparatus according to claim 20 wherein said means for producing a pulse includes a flip-flop which is set by said first counter and reset by said second counter.

22. Apparatus for detecting an out-of-round condition in a container, comprising:
  an oscillator,
  a transducer for generating an acoustic signal in response to said oscillator, said transducer including means for directing the acoustic signal towards a surface of the container,
  means for causing relative rotation between the container and signal,
  a second transducer for detecting an acoustic signal reflected from the surface of the container and generating an output signal in response to the received acoustic signal,
  means for computing variations in the phase difference between the oscillator signal and the output signal,
  means for detecting the maximum and minimum values of said variations in phase difference between the oscillator and output signals,
  means for detecting the difference between said maximum and minimum values, and
  means for comparing the difference between the maximum and minimum values to a pre-established threshold value representative of an excessive out-of-round condition.

23. Apparatus in accordance with claim 22 wherein said means for computing the value of the phase difference between the oscillator signal and the output signal includes a first counter for maintaining a count based on the oscillator signal, a second counter for maintaining a count based on the output signal, a flip-flop which is alternately set by said first counter and reset by said second counter, and means for integrating the output of the flip-flop to provide a signal indicative of said variations in phase difference.

24. Apparatus according to claim 23 including means for detecting the presence of said container at a test area, and means for resetting the output of said means for detecting the difference between said maximum and minimum values if said container is not present at said test area.

25. Apparatus for detecting an out-of-round condition in a container, comprising:
  means for directing a transmitter pulse signal towards a surface of the container, said pulse signal being reflected by said surface,
  means for causing relative rotation between the container and signal,
  means for receiving the signal reflected from the surface of the container,
  means for generating a variable pulse width signal based on the time of occurrence of said transmitter pulse signal and the time of reception of said reflected pulse signal,
  means for generating a variable amplitude signal based on said variable pulse width signal,
  means for detecting maximum and minimum peaks of said variable amplitude signal,
  means for detecting the difference between said maximum and minimum peaks, and
  means for comparing said difference between the maximum and minimum peaks to a pre-established threshold value representative of an excessive out-of-round condition.

26. The apparatus according to claim 25 wherein said means for generating said variable pulse width signal includes means for reducing the frequency of the received reflected pulse signal by a factor N to increase the range over which said variable pulse width signal is generated despite variations in the time of reception of said reflected pulse signal relative to the time of occurrence of said transmitter pulse signal.

27. Method of detecting an out-of-round condition in a container, comprising:
  directing a transmitter pulse signal towards a surface of the container, said pulse signal being reflected by said container surface,
  causing relative rotation between the container and signal, receiving the signal reflected from the surface of the container, generating a variable pulse width signal based on the time of occurrence of said transmitter pulse signal and the time of reception of said reflected pulse signal, generating a variable amplitude signal based on said variable pulse width signal, detecting maximum and minimum peaks of said variable amplitude signal, detecting the difference between said maximum and minimum peaks, and comparing said difference between the maximum and minimum peaks to a pre-established threshold value representative of an excessive out-of-round condition.

28. The method according to claim 27 wherein said step of generating a variable pulse width signal includes increasing the range over which said variable pulse width signal is generated by reducing the frequency of said received, reflected pulse signal by a factor N.

* * * * *